United States Patent
Bleiholder

(10) Patent No.: US 9,829,466 B2
(45) Date of Patent: Nov. 28, 2017

(54) APPROXIMATION ALGORITHM FOR SOLVING A MOMENTUM TRANSFER CROSS SECTION

(71) Applicant: Florida State University Research Foundation, Inc., Tallahassee, FL (US)

(72) Inventor: Christian Bleiholder, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 0 days.

(21) Appl. No.: 15/235,827

(22) Filed: Aug. 12, 2016

(65) Prior Publication Data

US 2016/0349212 A1    Dec. 1, 2016

Related U.S. Application Data

(63) Continuation of application No. PCT/US2015/016039, filed on Feb. 16, 2015.

(60) Provisional application No. 61/940,118, filed on Feb. 14, 2014.

(51) Int. Cl.
*G01N 23/20* (2006.01)
*H01J 49/04* (2006.01)
*G01N 27/62* (2006.01)
*H01J 49/00* (2006.01)
*H01J 49/40* (2006.01)

(52) U.S. Cl.
CPC .......... *G01N 27/622* (2013.01); *H01J 49/004* (2013.01); *H01J 49/0036* (2013.01); *H01J 49/40* (2013.01)

(58) Field of Classification Search
CPC ......... G01N 23/20058; G01N 23/2055; G01N 27/624; H01J 49/4295; H01J 49/0431

USPC ................................................ 250/282, 287
See application file for complete search history.

(56) References Cited

U.S. PATENT DOCUMENTS

| | | | |
|---|---|---|---|
| 5,719,392 A | 2/1998 | Franzen | |
| 6,124,592 A * | 9/2000 | Spangler | G01N 27/624 250/282 |
| 9,279,778 B2 * | 3/2016 | Beckman | G01N 23/2055 250/307 |
| 2004/0056191 A1 | 3/2004 | Jenkins et al. | |
| 2006/0219889 A1 | 10/2006 | Shvartsburg et al. | |
| 2010/0051800 A1 | 3/2010 | Atkinson | |
| 2012/0049057 A1 | 3/2012 | Wu et al. | |

FOREIGN PATENT DOCUMENTS

WO    2012109378 A2    8/2012

OTHER PUBLICATIONS

Bleiholder et al., A novel projection approximation algorithm for the fast and accurate computation of molecular collision cross sections (I). Method. International Journal of Mass Spectrometry. 2011. vol. 308: 1-10.

(Continued)

*Primary Examiner* — David A Vanore
(74) *Attorney, Agent, or Firm* — Eversheds Sutherland (US) LLP

(57) ABSTRACT

The present invention comprises a method for automated, high throughput molecular identification of macromolecular organic compounds. The method may provide an approximate solution to a momentum transfer cross section of an analyte in a buffer gas as measured by an ion mobility spectrometer that has low computational demand, has a high level of accuracy, and is adaptable for a variety of drift gases.

20 Claims, 6 Drawing Sheets

(56) References Cited

OTHER PUBLICATIONS

Bleiholder et al., A novel projection approximation algorithm for the fast and accurate computation of molecular collision cross sections (II). Model parameterization and definition of empirical shape factors for proteins. International Journal of Mass Spectrometry. 2013. vol. 345-347: 89-96.
Bleiholder et al., A novel projection approximation algorithm for the fast and accurate computation of molecular collision cross sections (III). Application to supramolecular coordination-drive assemblies with complex shapes. International Journal of Mass Spectrometry. 2012. vol. 330-332: 78-84.
Bleiholder et al., A novel projection approximation algorithm for the fast and accurate computation of molecular collision cross sections (IV). Application to polypeptides. International Journal of Mass Spectrometry. 2013. vol. 354-355: 275-280.
Wyttenbach et al., Factors contributing to the collision cross section of polyatomic ions in the kilodalton to gigadalton range: application to ion mobility measurements. Analytical Chemistry. 2013. vol. 85: 2191-2199.
International Search Report and Written Opinion for PCT/US2015/016039 (filed: Feb. 16, 2015) dated May 12, 2015; Applicant: The Florida State University Research Foundation, Inc.
International Preliminary Report on Patentability for PCT/US2015/016039 (filed: Feb. 16, 2015) dated Feb. 14, 2015; Applicant: The Florida State University Research Foundation, Inc.
Chinese Office Action for CN Application No. 201580008715.4 dated Mar. 24, 2017 (14 pages, including English translation).

\* cited by examiner

APPROXIMATION ALGORITHM FOR SOLVING A MOMENTUM TRANSFER CROSS SECTION

CROSS-REFERENCE TO RELATED APPLICATIONS

This nonprovisional application is a continuation of and claims priority to International Patent Application No. PCT/US2015/016039, entitled APPROXIMATION ALGORITHM FOR SOLVING A MOMENTUM TRANSFER CROSS SECTION", filed Feb. 16, 2015 by the same inventors, which claims priority to provisional U.S. Patent Application Ser. No. 61/940,118 filed on Feb. 14, 2014, titled, "Approximation Algorithm for Solving a Momentum Transfer Integral," which is hereby incorporated by reference in its entirety.

BACKGROUND OF THE INVENTION

1. Field of the Invention

This invention relates, generally, to ion mobility spectrometer analysis. More specifically, it relates to algorithms to approximate a solution to a momentum transfer cross section of an analyte in a buffer gas as measured by an ion mobility spectrometer.

2. Brief Description of the Prior Art

Ion mobility spectrometry (IMS) has been used for structural characterization of generally small organic and inorganic molecules. Recent advancement in the field have led to equipment modifications that allow IMS to be used for research involving large, macromolecular organic and biological compounds. IMS has shown particular usefulness in identifying macromolecular compounds related to a variety of illnesses and diseases. However, structure-elucidation of the compounds through IMS by comparison of IMS results of collision cross-sections with known, model molecular structures requires time-consuming and resource-intensive algorithms.

Several methods exist to approximate a solution to a momentum transfer cross section of an analyte in a buffer gas as measured by an ion mobility spectrometer in the low-field regime. However, none of the known methods combine low computational demand while providing a solution with a high degree of accuracy while also being adaptable for a plurality of drift gases. Four of the primary existing methods are described below.

The Trajectory Method (TM) simplifies the scattering problem by approximating the scattering potential energy surface by a sum of two-body interaction terms. The value of the momentum transfer cross section is then obtained by solving the Langrangian equations for a sufficiently large number of collision geometries on the potential energy surface and deducing the corresponding deflection angles. However, the scattering process of polyatomic ions in the drift cell is a many-body problem and exceedingly difficult to solve. Consequently, the computational demands to obtain a momentum transfer cross section for biological macromolecules are tremendous, and thus not applicable into high-throughput or molecular modeling software.

The Exact Hard Sphere Scattering (EHSS) approximation simplifies the two-body interaction potential to that of the collision of hard spheres with defined collision radius $R_{coll}$. The momentum transfer cross section is then obtained via ray tracing of the scattered trajectories and deducing the corresponding deflection angles. This method is not accurate enough for reliable assignment of molecular structure (due to the hard-sphere collision approximation), and further too time consuming for application into a high-throughput or molecular modeling software (due to the usage of ray tracing).

The Projection Approximation (PA) simplifies the scattering process by ignoring any interaction between the buffer gas and the analyte. Instead, it approximates the momentum transfer cross section as the orientation averaged area by determining the area enclosed by the analyte's atoms projected onto a plane for a plurality of orientations. This method is fast enough for incorporation into an automatic, high-throughput or molecular modeling software, but it's predicted values include errors of up to 20-30 percent due to neglect of buffer gas-analyte interactions, and thus is useless for structure assignment.

In the framework of the Projection Superposition Approximation (PSA), molecular collision cross-sections are computed as a projection approximation that is modified to account for buffer gas-analyte interactions and correct for shape-effects through a shape factor. It is consequently very accurate, but not as fast as necessary to be useful for incorporation into automated, structure-assignment software. Furthermore, this method ignores the molecular charge distribution and recent attempts to parameterize this method for nitrogen have shown that due to this approximation the predicted momentum transfer cross sections can be unreliable if the buffer gas is polarizable. It is anticipated that this method is therefore also unreliable for use with other strongly interacting drift gases, such as carbon monoxide or carbon dioxide.

Accordingly, what is needed is an algorithm to approximate a solution to a momentum transfer cross section of an analyte in a buffer gas as measured by an ion mobility spectrometer in the low-field regime that combines low computational demand while providing a solution with a high degree of accuracy while also being adaptable for a plurality of drift gases. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions, or is known to be relevant to an attempt to solve any problem with which this specification is concerned.

BRIEF SUMMARY OF THE INVENTION

Various embodiments may comprise a method for determining a molecular structure of an unknown analyte. Ion mobility mass spectrometry may be used to determine an ion mobility/mass spectrum for an unknown analyte. Using the ion mobility/mass spectrum, a molecular momentum transfer cross section may be calculated for the unknown analyte. A molecular momentum transfer cross section for each of a plurality of known compounds may be calculated. The calculation may involve calculating a potential energy function and calculating a momentum transfer function and calculating a momentum transfer surface in order to provide inputs for the actual calculation of the molecular momentum transfer cross section. Once the molecular momentum transfer cross sections have been calculated for the unknown analyte and a plurality of known compounds, a comparison can be made to determine if there is an approximate match between the molecular momentum transfer cross section of the unknown analyte and that of one or more of the known compounds. A potential identity of the unknown analyte may be determined based on the results of the comparison.

Additional embodiments may comprise a method for determining a molecular structure of an unknown analyte. A solution of the unknown analyte may be prepared as described previously. The solution may then be introduced into an ion mobility mass spectrometer to determine an ion mobility/mass spectrum for the unknown analyte. The ion mobility/mass spectrum may be observed to determine the presence of one or more peaks. A reduced ion mobility may then be calculated for each peak. Each reduced ion mobility value may be used to calculate a molecular momentum transfer cross section. In addition to the above analysis of the unknown analyte, molecular momentum transfer cross sections may be calculated for a plurality of known compounds. The calculation for the known compounds involves the following steps. First, a potential energy function may be calculated using Lennard-Jones 12,6 potentials and charge-induced interaction potential for a buffer gas particle. The potential energy function may be used to calculate a momentum transfer function. A molecular Boltzmann factor, an orientation-averaged cross section, a momentum transfer surface, and a shape-factor, respectively, may be calculated. The molecular momentum transfer cross section may be calculated for each known compound using at least the potential energy function, the molecular Boltzmann factor, the orientation-averaged cross section, the momentum transfer surface, and the shape-factor as inputs. The molecular momentum transfer cross section of the unknown analyte may be compared to the molecular momentum transfer cross sections of the known compounds. If an approximate match is found during the comparison step, then a potential identity of the unknown analyte may be determined.

Still further embodiments may comprise methods to quickly and efficiently determining a molecular momentum transfer cross section for a known compound. A potential energy function may be calculated using Lennard-Jones 12,6 potentials and charge-induced interaction potential for a buffer gas particle. The potential energy function may be used to calculate a momentum transfer function. A molecular Boltzmann factor for the compound may be calculated. An orientation-averaged cross section may be calculated, a momentum transfer surface may be calculated, and a shape-factor may be calculated. The molecular momentum transfer cross section may be calculated for the known compound using at least the potential energy function, the molecular Boltzmann factor, the orientation-averaged cross section, the momentum transfer surface, and the shape-factor as inputs.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figure 1:
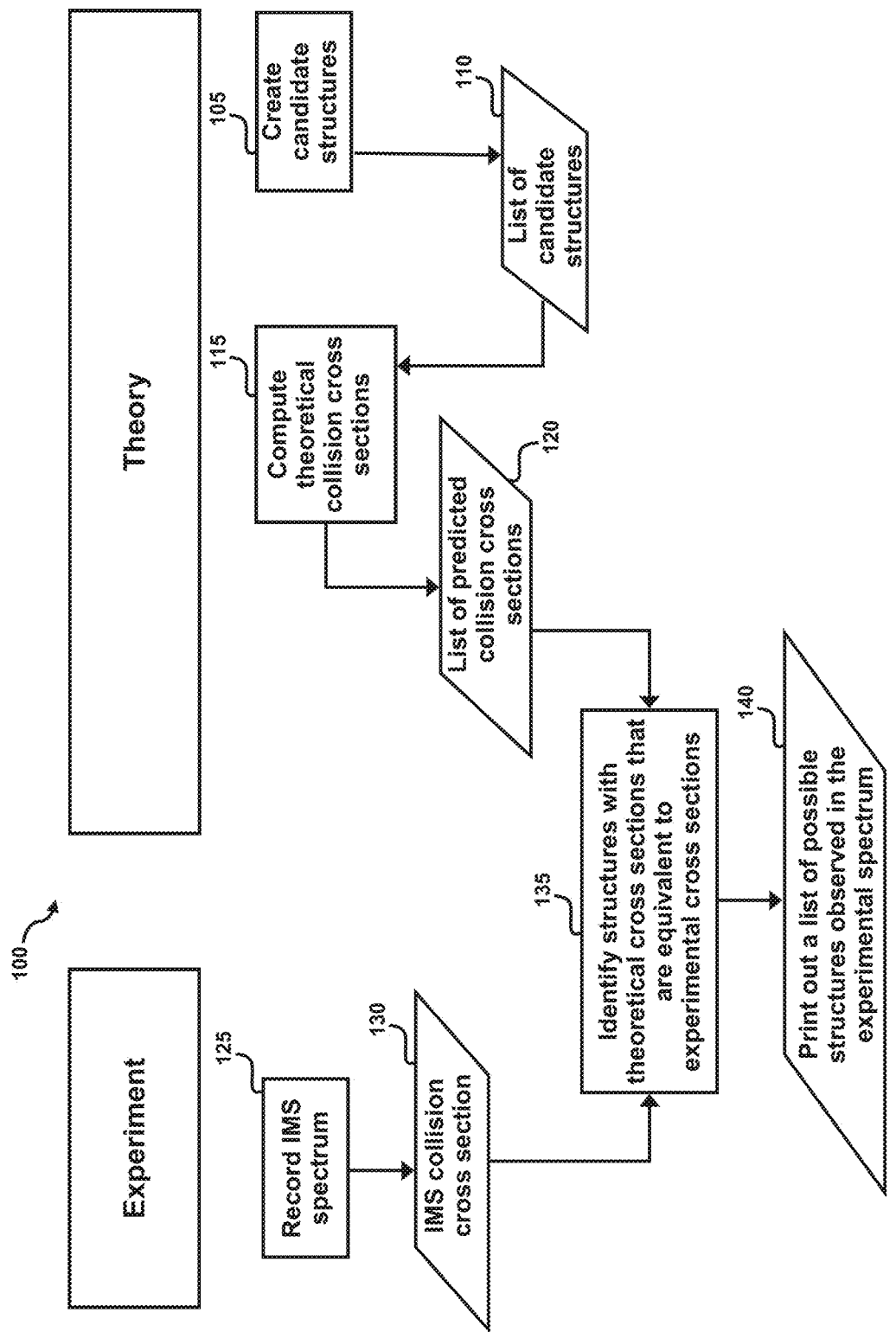
FIG. 1 is a general flow chart of a prior art method to identify a molecular structure of an unknown analyte.

Developments in the field of ion mobility spectrometry (IMS) have allowed IMS to be used for research and structural characterization involving large, macromolecular organic compounds. FIG. 1 illustrates a flow diagram of a prior art method 100 of a manual structural characterization divided into theoretical steps and experimental steps. First, a plurality of candidate structures are determined and a theoretical momentum transfer cross section may be computed for each candidate structure (steps 105 through 115). At step 120, a list of the predicted momentum transfer cross sections may be produced for future identification of unknown compounds (that is, create a database of theoretical momentum transfer cross sections for the candidate structures). At step 125, an analyte solution containing, for example, proteins, may be sampled by the IMS. The IMS may output an IMS spectrum that may comprise a graph of the collision cross-section comprising one or more peaks. At step 130, an IMS momentum transfer cross section may be calculated for the analyte. Traditionally, the peaks may be manually matched to known results to identify the composition of the analyte (step 135) and a list of possible structures may be produced (step 140). While this arrangement may be acceptable for laboratory analysis of a few samples, the manual nature of the structure-elucidation of the identified peaks does not lend itself to high throughput workflow situations.

In addition, currently known methods to compute the theoretical momentum transfer cross sections of candidate structures (step 115) are too computationally demanding to perform in a routine, high throughput manner, or are too inaccurate to enable reliable structure assignment to experimental collision cross determined for an unknown compound (step 135). These unacceptable current methods include the Trajectory Method, Exact Hard Sphere Scattering, Projection Approximation, and Projection Superposition Approximation.

According to various embodiments, a sample of the unknown analyte may be prepared by mixing the analyte with an appropriate solvent to form a solution of a desired concentration. For biomolecules, the solution may have a 1-50 μM concentration and the solvent may be water. The solution may also contain a volatile buffer such as ammonium acetate or bicarbonate, and may be adjusted for pH.

For situations in which an off-line nano-electrospray ionization source is coupled to the ion mobility mass spectrometer, typically 1-10 μL of the prepared solution may be loaded into gold coated nano-electrospray ionization capillaries and electrosprayed. For situations in which an online electrospray ionization source is coupled to the ion mobility mass spectrometer, typically 10-100 μL of the prepared solution may be loaded into a gastight syringe and directly infused into an electrospray ionization source by means of a syringe pump. Other ionizations methods as known in the art may also be used.

Figure 2:
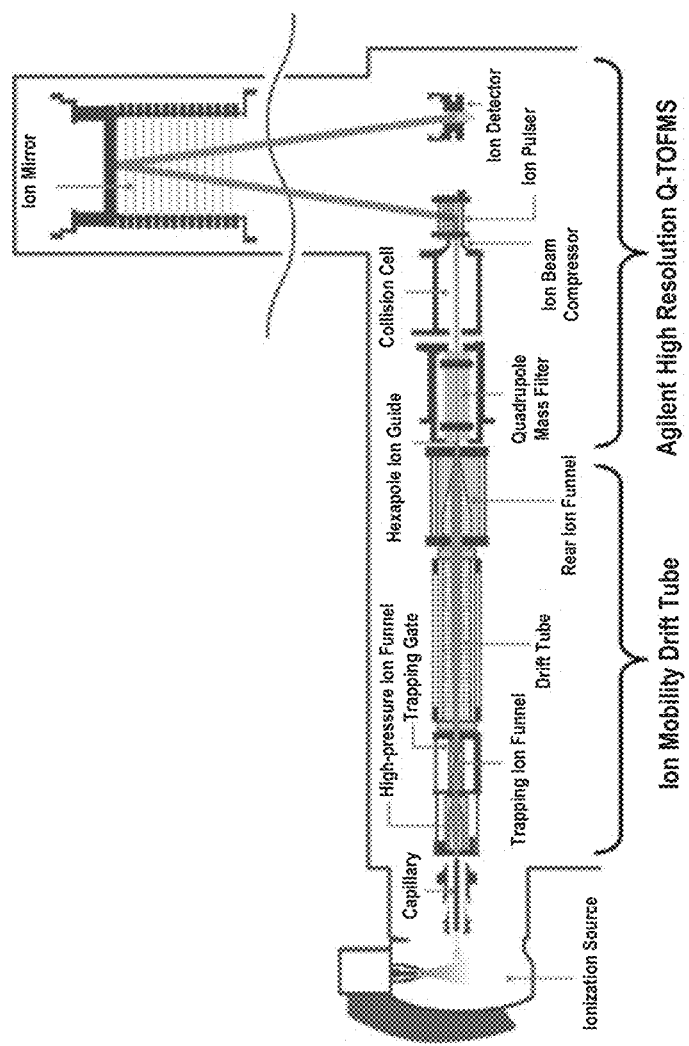
FIG. 2 is a schematic diagram of an ion mobility mass spectrometer.

The ion mobility mass spectrometer (see FIG. 2) may be set up selecting the appropriate experimental parameters. In various embodiments, the parameters may include the following: (1) ion mode (negative versus positively charged ions); (2) a variety of voltage and pressures in different components of the ion mobility mass spectrometer, including the ion mobility device; (3) drift gas (for example, helium or nitrogen), gas temperature, gas pressure; and (4) voltage.

Analyte ions may be created when an operator turns on the ion source and transfers the analyte into the ion mobility mass spectrometer through a capillary or small orifice. When a commercially available instrument is used, typically a two-dimensional ion mobility/mass spectrum may be obtained in which each data point I(m/z, $t_d$), which corresponds to the abundance of an ion with mass-to-charge ratio m/z and drift time $t_d$, is recorded. The mass-to-charge ratio m/z may be determined by a mass analyzer of the instrument (such as a time-of-flight mass or quadrupole mass analyzer). The drift time $t_d$ may be determined by the ion mobility analyzer of the instrument.

Figure 3:
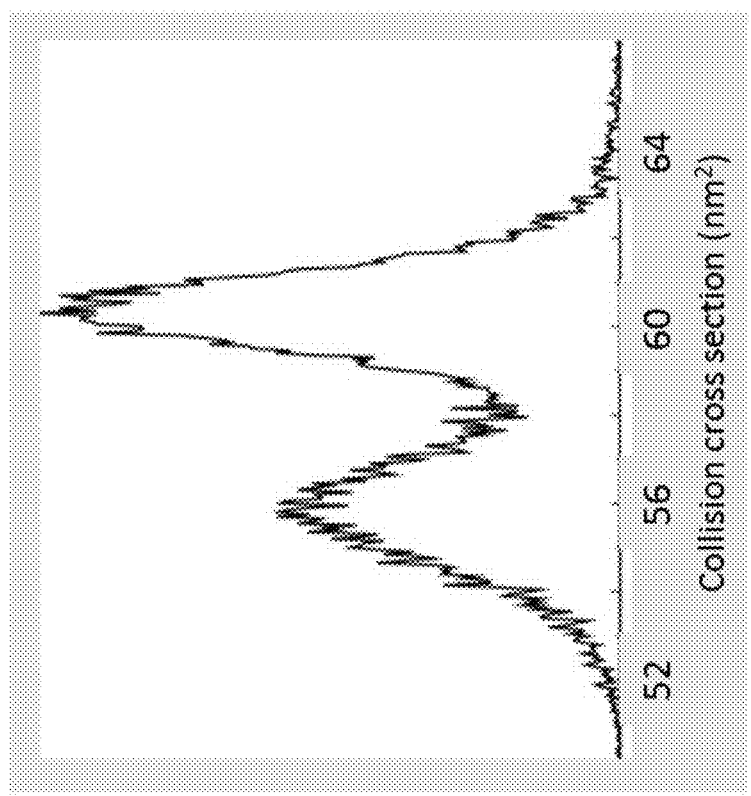
FIG. 3 is an exemplary graph of output data from an ion mobility mass spectrometer.

When using a non-commercial instrument, the operator may be required to manually select a number of specific mass-to-charge ratios m/z and record a one-dimensional ion mobility/mass spectrum I(m/Z, $t_d$) for each of the selected mass-to-charge ratios m/z (see FIG. 3). With either type of instrument, the operator may vary the parameters of the ion mobility component, such as voltage, gas temperature, or gas pressure.

The ion mobility/mass spectrum may then be analyzed to determine a number of positions $I_{max}$(m/z, $t_d$) where the ion mobility/mass spectrum I(m/z, $t_d$) displays maximum abundances. A reduced ion mobility $K_0$ may be determined for specific m/z values from the drift time $t_d$ and the mass-to-charge ratio m/z of any such maximum $I_{max}$(m/Z, $t_d$). The molecular momentum transfer cross section Ω(T) may be determined from the reduced ion mobility $K_0$ according to Equation 1:

$$\Omega(T) = \frac{3Ze}{16N_0} \sqrt{\frac{2\pi}{\mu k_B T}} \cdot \frac{1}{K_0} \qquad \text{Eqn. 1}$$

The molecular momentum transfer cross section Ω(T) may then be used to determine the molecular structure of the analyte ion by comparison to values for known compounds.

Various embodiments may comprise one or more algorithms to automate the peak identification process. A database of candidate structures may be created, from which a list of candidate structures may be obtained. The theoretical collision cross-sections of the candidate structures may be computed, and then a list of predicted collision cross-sections may be produced. The IMS peak outputs may be compared to the list of predicted collision cross-sections to identify structures with theoretical cross-sections equivalent to the IMS peaks. An output may be produced listing possible structures that fit the IMS peaks.

Current known methods of computing the theoretical collision cross-sections demand high levels of computational demand that are impractical for routine, high throughput use, or are too inaccurate to enable reliable structure assignment to experimental cross-sections (IMS peaks). Various embodiments as described herein provide higher accuracy and reduced computational demand such that an automated system to analyze a large number of analytes in a short period of time may be developed.

Various embodiments comprise an algorithm to give an approximate solution to the momentum transfer cross section Ω of an analyte in a buffer gas as measured by an ion mobility spectrometer in the low-field regime according to Equation 2:

$$\Omega(T) = 2\pi \int_0^\infty f(\delta,T) \int_0^\pi (1-\cos\theta)\sigma(\epsilon,\theta)\sin\theta d\theta d\epsilon \qquad \text{Eqn. 2}$$

where Ω(T) is the momentum transfer cross section of the analyte ion due to collisions with the buffer gas at temperature T occurring in the drift cell of an ion mobility spectrometer, $\epsilon$ is the kinetic energy, $\theta$ is the deflection angle, f($\epsilon$,T) is the Boltzmann distribution of the kinetic energy $\epsilon$ for an analyte ion—buffer gas system at temperature T, and $\sigma(\epsilon,\theta)$ is the differential momentum transfer cross section for collisions with kinetic energy $\epsilon$.

Various embodiments of the algorithm may comprise an input defined as a molecular structure. The molecular structure may comprise x, y, z coordinates of atomic positions, charge, and element number for every atom contained in the molecule. A molecular energy potential is then defined based on two-body interaction terms. The two-body interaction terms may be fitted to temperature-dependent data on model compounds, and can be in a form similar to a Lennard-Jones potential.

A potential energy function $U(\vec{r})$ may be defined for that geometry which describes the interaction potential between the molecular analyte ion and the buffer gas particle at position $\vec{r}$ by Equation 3:

$$U(\vec{r}) = \Sigma_{l=1}^{atoms} u_l(\vec{r}) + V(\vec{r}) \qquad \text{Eqn. 3}$$

The function $u_l(\vec{r})$ may be essentially identical to a (standard) Lennard-Jones 12,6 potential with parameters E and $r_m$ centered at the origins of the atoms $\vec{R_l}$ according to Equation 4:

$$u_l(\vec{r}) = E\left[\left(\frac{r_m}{|\vec{r}-\vec{R_l}|}\right)^{12} - \left(\frac{r_m}{|\vec{r}-\vec{R_l}|}\right)^6\right] \qquad \text{Eqn. 4}$$

The function $V(\vec{r})$ may be identical to the (standard) charge-induced interaction potential for a buffer gas particle with polarizability α, centered at the origins of the atoms $\vec{R}$.

The Lennard-Jones parameters E, $r_m$ that define the functions $u_i(\vec{r})$ for different elements and the polarizability α that defines $V(\vec{r})$ for different buffer gases may be taken from the literature.

A momentum transfer function $\tau(\epsilon, \vec{r})$ may be defined by Equation 5:

$$\tau(\varepsilon, \vec{r}) = \frac{1}{1 + \left[\frac{\varepsilon - U(\vec{r})}{\pi \cdot U(\vec{r})}\right]^4} \quad \text{Eqn. 5}$$

The function $\tau(\epsilon, \vec{r})$ may define the likelihood that a collision occurs at position $\vec{r}$ given a kinetic energy E. The function $U(\vec{r})$ may be the molecular interaction potential defined in Equation 3.

Given the momentum transfer function $\tau(e, \vec{r})$, the momentum transfer cross section $\Omega(T)$ is computed as shown in Equation 6:

$$\Omega(T) = \int_0^\infty f(\epsilon,T) \cdot \xi[\tau(\epsilon,\vec{r})] \cdot \rho[S[\tau(\epsilon,\vec{r})]] d\epsilon \quad \text{Eqn. 6}$$

Where $f(\epsilon, T)$ is the molecular Boltzmann factor described above; $\xi[\tau(\epsilon,\vec{r})]$, $S[\tau(\epsilon,\vec{r})]$, and $\rho[S[\tau(\epsilon,\vec{r})]]$ are the orientation-averaged cross section, momentum transfer cross section, and shape-factor for kinetic energy $\epsilon$, respectively, and are functionals of the momentum transfer function $\tau(\epsilon, \vec{r})$.

The orientation-averaged cross section $\xi[(\epsilon, \vec{r})]$ for kinetic energy $\epsilon$ may be computed as the asymptotic average of orientation-aligned cross sections $\sigma(\epsilon, \vec{z_k})$ for kinetic energy $\epsilon$ by Equation 7:

$$\xi[\tau(\varepsilon, \vec{r})] = \lim_{n \to \infty} \frac{1}{n} \sum_{k=1}^{n} \sigma(\varepsilon, \vec{z_k}) \quad \text{Eqn. 7}$$

Where $\vec{z_k}$ denotes the randomly chosen orientation.

A single oriented-aligned cross section $\sigma(\epsilon, \vec{z_k})$ for kinetic energy s may be computed as shown in Equation 8:

$$\sigma(\varepsilon, \vec{z_k}) = A \frac{n_{coll}}{n_{coll} + n_{miss}} \quad \text{Eqn. 8}$$

Where A is the area of a bounding box in a plane with normal vector $\vec{z_k}$ that fully contains the molecule. The quantities $n_{coll}$ and $n_{miss}$ are obtained by ray-casting from a point $\vec{r_A}$ within area A along $\vec{z_k}$ and denote the number of rays $\vec{r}(s) = \vec{r_A} + s \cdot \vec{z_k}$ that are considered a "collision" ($n_{coll}$) and "no collision" ($n_{miss}$), respectively, according to the Monte Carlo criterion $p \leq \tau(\epsilon, \vec{r_A} + s \cdot \vec{z_k})$, where p is a random number.

The points $\vec{r}(s)$ for which $p \leq \tau(\Sigma, \vec{r_A} + s \cdot \vec{z_k})$ was true (above) may then be used to define a momentum transfer surface S with $S[\tau(\epsilon,\vec{r})] = \{\vec{r}(s) | p \leq \tau(\epsilon, \vec{r}(s))\}$.

The shape-factor $\rho[S[\tau(\epsilon,\vec{r})]]$ is then computed by Equation 9:

$$\rho[S[\tau(\varepsilon, \vec{r})]] = \frac{A(S[\tau(\varepsilon, \vec{r})])}{C(S[\tau(\varepsilon, \vec{r})])} \quad \text{Eqn. 9}$$

Here, $C(S[\tau(\epsilon,\vec{r})])$ denotes the area of the convex hull of the momentum transfer surface $S[\tau(\epsilon,\vec{r})]$ and $A(S[\tau(\epsilon,\vec{r})])$ is computed according to Equation 10:

$$A(S[\tau(\varepsilon, \vec{r})]) = \lim_{\alpha \to 0} A(\alpha, S[\tau(\varepsilon, \vec{r})]) \quad \text{Eqn. 10}$$

Where $A(\alpha, S[\tau(\epsilon,\vec{r})])$ is the exposed surface area of a Delaunay triangulation of momentum transfer surface $S[\tau(\epsilon,\vec{r})]$ in which all tetrahedrons with side lengths greater than a have been disregarded.

The quantities $f(\epsilon, T)$, $\xi[\tau(\epsilon,\vec{r})]$, and $\rho[S[\tau(\epsilon,\vec{r})]]$ may then be integrated according to Equation 6 in order to compute the molecular momentum transfer cross section $\Omega(T)$.

Figure 4:
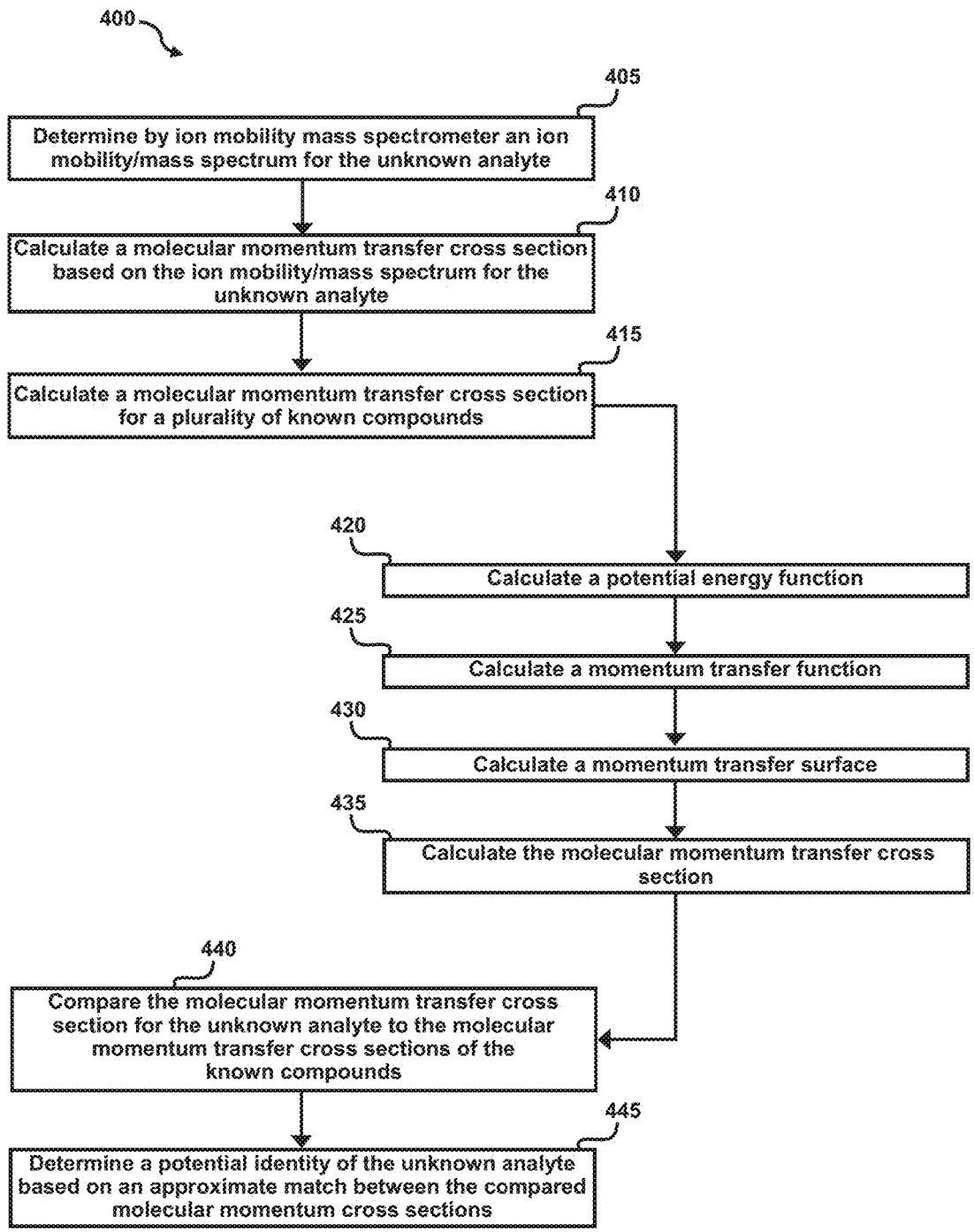
FIG. 4 is an exemplary flow chart of a method for determining a molecular structure of an unknown analyte.

FIG. 4 illustrates a general flow chart of various embodiments of a method 400 for determining a molecular structure of an unknown analyte. Ion mobility mass spectrometry may be used to determine an ion mobility/mass spectrum for an unknown analyte at step 405. Using the ion mobility/mass spectrum, at step 410 a molecular momentum transfer cross section may be calculated for the unknown analyte. At step 415, a molecular momentum transfer cross section for each of a plurality of known compounds may be calculated. The calculation of step 415 may involve calculating a potential energy function (step 420), calculating a momentum transfer function (step 425), and calculating a momentum transfer surface (step 430) in order to provide inputs for the actual calculation of the molecular momentum transfer cross section (step 435). Once the molecular momentum transfer cross sections have been calculated for the unknown analyte and a plurality of known compounds, a comparison can be made to determine if there is an approximate match between the molecular momentum transfer cross section of the unknown analyte and that of one or more of the known compounds (step 440). At step 445, a potential identity of the unknown analyte may be determined based on the results of the comparison.

Figure 5:
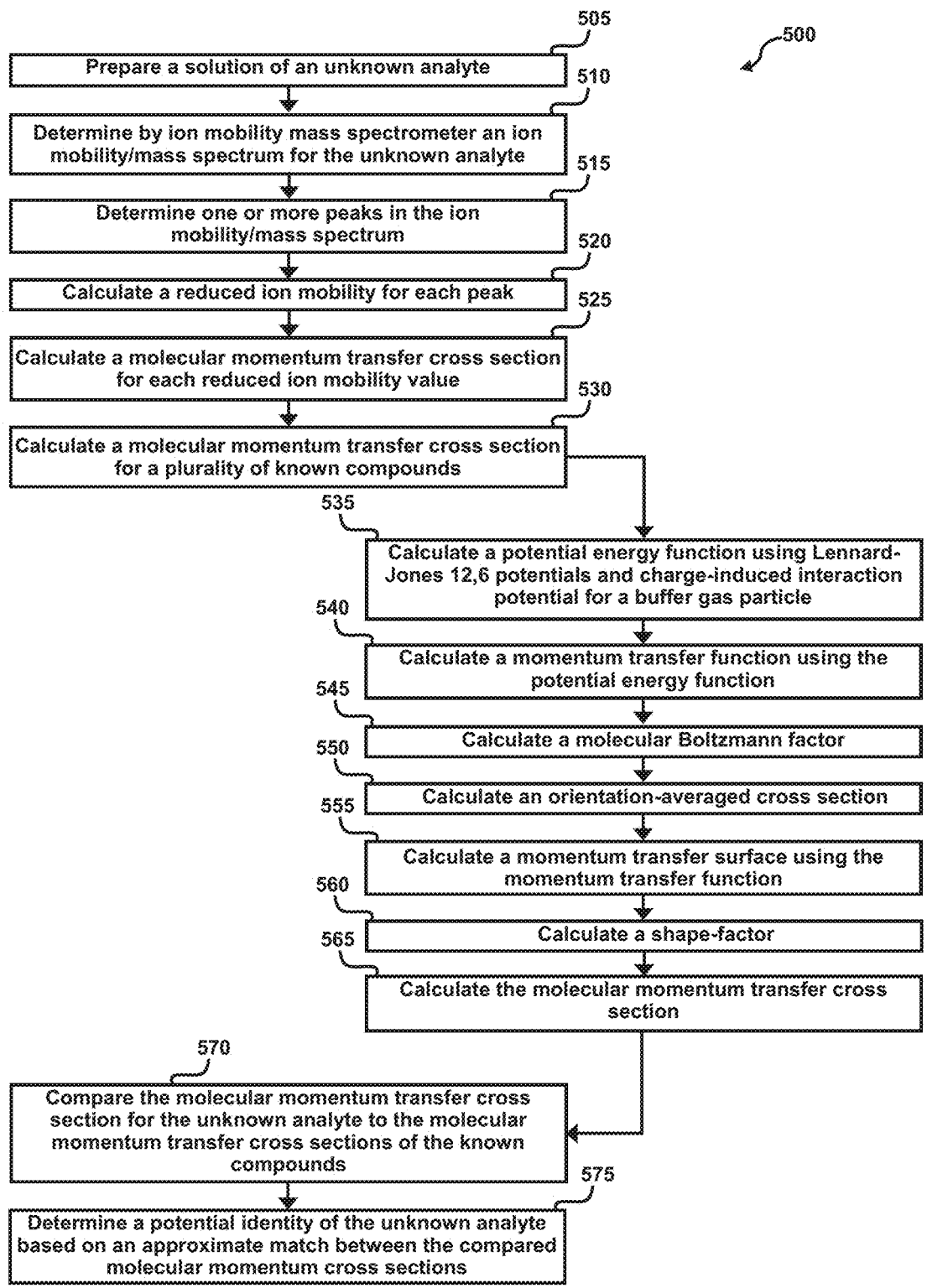
FIG. 5 is an exemplary flow chart of a method for determining a molecular structure of an unknown analyte.

FIG. 5 illustrates another general flow chart of various embodiments of a method 500 for determining a molecular structure of an unknown analyte. At step 505, a solution of the unknown analyte may be prepared as described previously. The solution may then be introduced into an ion mobility mass spectrometer at step 510 to determine an ion mobility/mass spectrum for the unknown analyte. At step 515, the ion mobility/mass spectrum may be observed to determine the presence of one or more peaks. A reduced ion mobility may then be calculated at step 520 for each peak. At step 525, each reduced ion mobility value may be used to calculate a molecular momentum transfer cross section. In addition to the above analysis of the unknown analyte, molecular momentum transfer cross sections may be calculated for a plurality of known compounds (steps 530 through 565). The calculation for the known compounds involves the following steps. First, at step 535, a potential energy function may be calculated using Lennard-Jones 12,6 potentials and charge-induced interaction potential for a buffer gas particle. A step 540, the potential energy function may be used to calculate a momentum transfer function. At steps 545, 550, 555, and 560, a molecular Boltzmann factor, an orientation-averaged cross section, a momentum transfer surface, and a shape-factor, respectively, may be calculated. At step 565, the molecular momentum transfer cross section may be calculated for each known compound using at least the potential energy function, the molecular Boltzmann factor, the orientation-averaged cross section, the momentum transfer surface, and the shape-factor as inputs. At step 570, the molecular momentum transfer cross section of the unknown analyte may be compared to the molecular momentum transfer cross sections of the known compounds. If an approximate match is found during the comparison step, then a potential identity of the unknown analyte may be determined at step 575.

Figure 6:
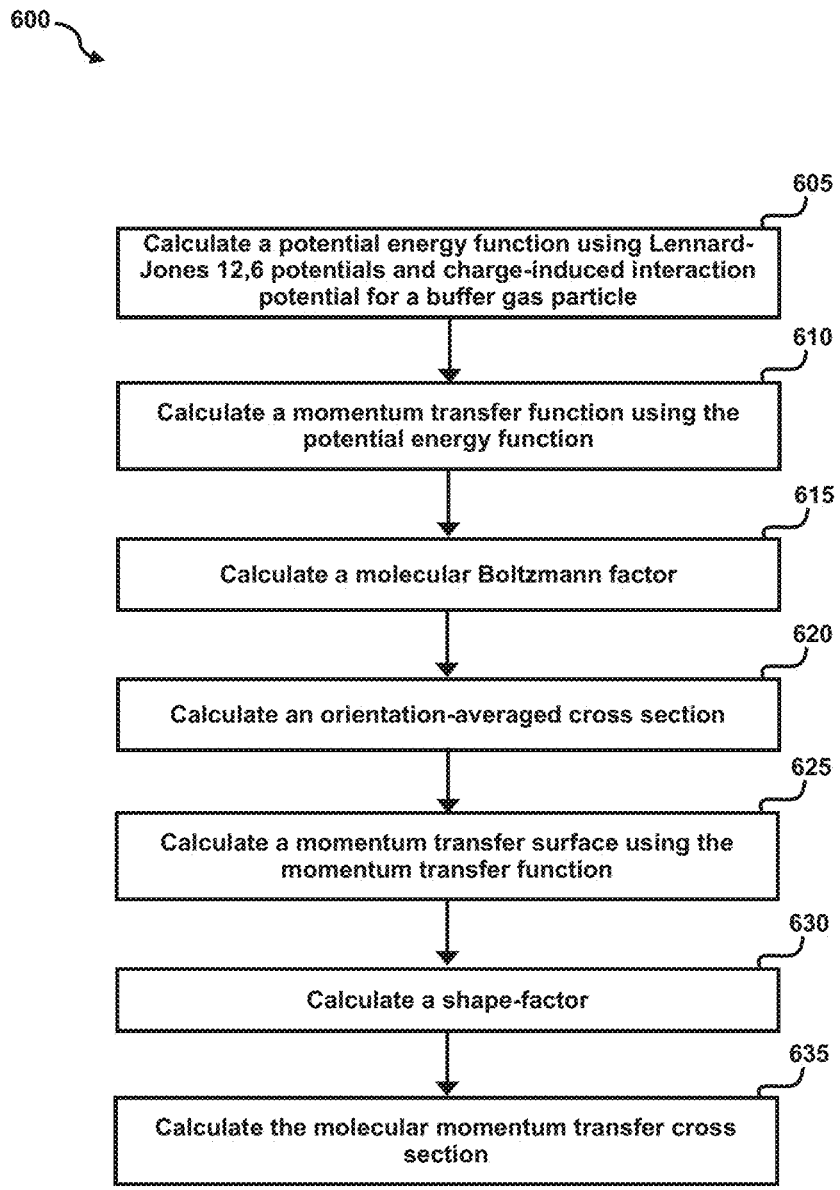
FIG. 6 is an exemplary flow chart of a method for determining a molecular momentum transfer cross section for a known compound.

FIG. 6 illustrates a general flow diagram of various embodiments for a method 600 to quickly and efficiently determining a molecular momentum transfer cross section for a known compound. At step 605, a potential energy function may be calculated using Lennard-Jones 12,6 potentials and charge-induced interaction potential for a buffer gas particle. At step 610, the potential energy function may be used to calculate a momentum transfer function. A molecular Boltzmann factor for the compound may be calculated at step 615. An orientation-averaged cross section may be calculated at step 620, and a momentum transfer surface may be calculated using the momentum transfer function at step 625. A shape-factor may be calculated at step 630. At step 635, the molecular momentum transfer cross section may be calculated for each known compound using at least the potential energy function, the molecular Boltzmann factor, the orientation-averaged cross section, the momentum transfer surface, and the shape-factor as inputs.

Various embodiments may be stored or implemented on computer readable medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Programs embodied on a computer readable medium may be transmitted using any appropriate medium, including but not limited to wireless, wire-line, optical fiber cable, radio frequency, etc., or any suitable combination of the foregoing. Computer programs for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Glossary of Claim Terms

Buffer gas: A gas present in a drift tube of an ion mobility mass spectrometer that opposes ion motion.

Charge-induced interaction potential: The propensity for movement of two particles relative to one another to be affected by the charge of those particles.

Ion mobility mass spectrometer: An instrument that produces a two-dimensional separation in which gas phase ions of the same ion mobility are separated in the mass domain and ions of the same mass are separated in the ion mobility domain. The instrument may comprise an ion source to generate ions an ion mobility chamber positioned to receive the ions from the ion source.

Ion mobility/mass spectrum: A two-dimensional graph of data generated by an ion mobility mass spectrometer in which each data point corresponds to an abundance of ions with a given mass-to-charge ratio and drift time.

Lennard-Jones 12,6 potential: A mathematical approximation of the interaction between a pair of neutral atoms or molecules.

Low-field regime: An operating regime for an ion mobility mass spectrometer in which the momentum-gain due to the electric field is balanced by momentum-loss due to collisions occurring in a drift cell of an ion mobility mass spectrometer between an analyte and a buffer gas at temperature T.

Molecular Boltzmann factor: The molecular thermal kinetic energy probability distribution, ratio of a Boltzmann distribution for two states, and characteristically only depends on the states' energy difference. A Boltzmann distribution is a probability distribution, probability measure, or frequency distribution of particles in a system over various possible states.

Molecular momentum transfer cross section: This expression is used as a synonym to other commonly used terms (e.g., collision cross section, collision integral, momentum transfer integral) to express the effective area of an analyte ion when momentum is transferred between an analyte ion and a buffer gas at temperature T due to collisions occurring in a drift cell of an ion mobility mass spectrometer.

Momentum transfer function: A function that defines the likelihood that a collision occurs at a given position at a given kinetic energy.

Momentum transfer surface: a set of points $\vec{r}$ at which a collision is said to occur according to the Monte-Carlo criterion $p \leq \tau(\epsilon, \vec{r})$, where p is a random number and $\tau(\epsilon, \vec{r})$ is the momentum transfer function.

Orientation-averaged cross section: The asymptotic average of orientation-aligned cross sections.

Peak: With respect to an ion mobility/mass spectrum, the peaks of the graphical representation of the spectrum data.

Potential energy function: Describes the interaction potential between a molecular analyte ion and a buffer gas particle at a given position.

Reduced ion mobility: The ion mobility on an analyte under a standard number density N of the buffer gas, typically for number density N at a pressure p=760 torr and T=273.15K.

Shape-factor: A measure of the concaveness of a molecule relative to a purely convex molecule of the same size and is essentially the ratio of the actual molecular surface area of a molecule to the surface area of the convex envelope of the molecule.

What is claimed is:

1. A method for determining a molecular structure of an analyte, comprising:
    determining by ion mobility mass spectrometer an ion mobility/mass spectrum for an unknown analyte;
    calculating a molecular momentum transfer cross section based on the ion mobility/mass spectrum for the unknown analyte;
    calculating, for each of a plurality of known compounds, a molecular momentum transfer cross section according to the following steps:
        calculating a potential energy function;
        calculating a momentum transfer function using the potential energy function;
        calculating a momentum transfer surface using the momentum transfer function;
        calculating the molecular momentum transfer cross section for each known compound using the momentum transfer function; and
    comparing the molecular momentum transfer cross section for the unknown analyte to the molecular momentum transfer cross sections of the plurality of known compounds, and reporting a potential identity of the unknown analyte by an approximate match of the compared molecular momentum transfer cross sections.

2. The method of claim 1, further comprising determining one or more peaks in the ion mobility/mass spectrum.

3. The method of claim 2, further comprising calculating a reduced ion mobility for each peak.

4. The method of claim 3, wherein calculating the molecular momentum transfer cross section for the unknown analyte is based on the reduced ion mobility for each peak.

5. The method of claim 1, wherein calculating the potential energy function comprises using Lennard-Jones 12,6 potentials and charge-induced interaction potential for a buffer gas particle.

6. The method of claim 1, wherein calculating the molecular momentum transfer cross section for each known compound using the momentum transfer function further comprises using a molecular Boltzmann factor, an orientation-averaged cross section, and a shape-factor in the calculation.

7. The method of claim 1, wherein calculating the momentum transfer surface comprises determining a set of points defined as a function of a number of rays that are considered a collision and a number of rays considered no collision, and the momentum transfer function.

8. The method of claim 1, further comprising creating a database of the molecular momentum transfer cross sections of the plurality of known compounds.

9. The method of claim 1, wherein the ion mobility mass spectrometer determination is performed in a low-field regime.

10. The method of claim 1, wherein calculating the molecular momentum transfer cross section comprises approximating the thermal average of the momentum transferred between an analyte ion and a buffer gas due to collisions occurring in the ion mobility mass spectrometer.

11. The method of claim 1, wherein the calculation of the molecular momentum transfer cross section of each of the known compounds is based at least in part on a plurality of input molecular structures each corresponding to a respective one of the known compounds, and wherein each of the input molecular structures comprises x, y, z coordinates of atomic positions, charge, and element number for each atom contained in a respective one of the known compounds.

12. A method for determining a molecular structure of an analyte, comprising:
    preparing a solution of an unknown analyte;
    determining by ion mobility mass spectrometry an ion mobility/mass spectrum for the unknown analyte;
    determining one or more peaks in the ion mobility/mass spectrum;
    calculating a reduced ion mobility for each peak;
    calculating a molecular momentum transfer cross section for each reduced ion mobility value;
    calculating, for each of a plurality of known compounds, a molecular momentum transfer cross section according to the following steps:

calculating a potential energy function using Lennard-Jones 12,6 potential and charge-induced interaction potential for a buffer gas particle;

calculating a momentum transfer function using the potential energy function;

calculating a molecular Boltzmann factor;

calculating an orientation-averaged cross section;

calculating a momentum transfer surface using the momentum transfer function;

calculating a shape-factor;

calculating the molecular momentum transfer cross section using the momentum transfer function, the molecular Boltzmann factor, the orientation-averaged cross section, and the shape-factor; and comparing the molecular momentum transfer cross section for the unknown analyte to the molecular momentum transfer cross sections of the plurality of known compounds, and reporting a potential identity of the unknown analyte by an approximate match of the compared molecular momentum transfer cross sections.

13. The method of claim 12, wherein calculating the momentum transfer surface comprises determining a set of points defined as a function of a number of rays that are considered a collision and a number of rays considered no collision, and the momentum transfer function.

14. The method of claim 12, further comprising creating a database of the molecular momentum transfer cross sections of the plurality of known compounds.

15. The method of claim 12, wherein comparing the molecular momentum transfer cross sections comprises comparing the molecular momentum transfer cross section for each peak in the ion mobility/mass spectrum.

16. The method of claim 12 wherein the ion mobility mass spectrometer determination is performed in a low-field regime.

17. The method of claim 12, wherein calculating the molecular momentum transfer cross section comprises approximating the thermal average of the momentum transferred between an analyte ion and a buffer gas due to collisions occurring in the ion mobility spectrometer.

18. The method of claim 12, wherein the calculation of the molecular momentum transfer cross section of each of the known compounds is based at least in part on a plurality of input molecular structures each corresponding to a respective one of the known compounds, and wherein each of the input molecular structures comprises x, y, z coordinates of atomic positions, charge, and element number for each atom contained in a respective one of the known compounds.

19. A method for determining a molecular momentum transfer cross section, comprising:

calculating a potential energy function using Lennard-Jones 12,6 potential and charge-induced interaction potential for a buffer gas particle;

calculating a momentum transfer function using the potential energy function;

calculating a molecular Boltzmann factor;

calculating an orientation-averaged cross section;

calculating a momentum transfer surface using the momentum transfer function calculating a shape-factor; and calculating the molecular momentum transfer cross section using the momentum transfer function, the molecular Boltzmann factor, the orientation-averaged cross section, and the shape-factor.

20. The method of claim 19, wherein wherein calculating the momentum transfer surface comprises determining a set of points defined as a function of a number of rays that are considered a collision and a number of rays considered no collision, and the momentum transfer function.

* * * * *